United States Patent
Murata et al.

(10) Patent No.: US 9,120,833 B2
(45) Date of Patent: Sep. 1, 2015

(54) POLYFLUOROALKYLPHOSPHONIC ACID ESTER AND PROCESS FOR PRODUCING THE SAME

(75) Inventors: Seiichiro Murata, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 217 days.

(21) Appl. No.: 13/383,299

(22) PCT Filed: Jun. 23, 2010

(86) PCT No.: PCT/JP2010/060621
§ 371 (c)(1),
(2), (4) Date: Jan. 10, 2012

(87) PCT Pub. No.: WO2011/004705
PCT Pub. Date: Jan. 13, 2011

(65) Prior Publication Data
US 2012/0108849 A1 May 3, 2012

(30) Foreign Application Priority Data
Jul. 10, 2009 (JP) .................................. 2009-163257

(51) Int. Cl.
*C07F 9/02* (2006.01)
*C07F 9/40* (2006.01)

(52) U.S. Cl.
CPC .................................. *C07F 9/4006* (2013.01)

(58) Field of Classification Search
None
See application file for complete search history.

(56) References Cited

U.S. PATENT DOCUMENTS 3,600,475 A 8/1971 Schimmelschmidt

FOREIGN PATENT DOCUMENTS

| JP | 51-18417 | 6/1976 |
|---|---|---|
| JP | 58-180597 | 10/1983 |
| JP | 59-166596 | 9/1984 |
| JP | 60-190309 | 9/1985 |
| JP | 60-193615 | 10/1985 |
| WO | WO03/102003 A1 | 12/2003 |
| WO | WO 2007/105633 A1 | 9/2007 |

OTHER PUBLICATIONS

Wroblewska, A et al. Journal of Fluorine Chemistry (2006), 127(3), 345-350; Derwent abstract provided.*
International Preliminary Report on Patentability and Written Opinion from corresponding PCT application No. PCT/JP2010/060621 dated Feb. 12, 2012 (9 pgs).
International Search Report from corresponding PCT application No. PCT/JP2010/060621 dated Jul. 20, 2010 (4 pgs).
European Search Report from corresponding European application No. 10797016.2 dated Dec. 13, 2012 (9 pgs).
Ivin S Z et al., Reactions of Dialkyl Phosphites and Alkyl Phosphonites with Perfluoro-Propylene under the Influence of Gamma-Irradiation:, Journal of Applied Chemistry of USSR, Consultants Bureau, New York, NY, US, vol. 42, Jan. 1, 1969, pp. 444-445, XP009164622, ISSN: 0021-888X, p. 445, table 1.
Tumanskii B L. et al., Free-Radical Addition of Dialkyl Phosphites to Branched Fluoro-Olefines:, Phosphorus, Sulfur and Silicon and the Related Elements, Taylor & Francis Inc., US, vol. 51/52, Jan. 1, 1990, p. 668, XP009164621, ISSN: 01042-6507 p. 198.

* cited by examiner

*Primary Examiner* — Clinton Brooks
(74) *Attorney, Agent, or Firm* — Brinks Gilson & Lione

(57) ABSTRACT

A polyfluoroalkylphosphonic acid ester represented by the general formula: $C_nF_{2n+1}(CH_2CF_2)_a(CF_2CF_2)_b(CH_2CH_2)_cP(O)(OR)_2$ (R is an alkyl group having 1 to 4 carbon atoms, n is an integer of 1 to 6, a is an integer of 1 to 4, b is an integer of 1 to 3, and c is an integer of 1 to 3) is produced by a process of reacting a polyfluoroalkyl iodide represented by the general formula: $C_nF_{2n+1}(CH_2CF_2)_a(CF_2CF_2)_b(CH_2CH_2)_cI$ with a trialkyl phosphite represented by the general formula: $P(OR)_3$ or by a process of reacting a polyfluoro-1-alkene represented by the general formula: $C_nF_{2n+1}(CH_2CF_2)_a(CF_2CF_2)_bCH=CH_2$ with a dialkyl phosphite represented by the general formula: $(RO)_2P(O)H$.

3 Claims, No Drawings

POLYFLUOROALKYLPHOSPHONIC ACID ESTER AND PROCESS FOR PRODUCING THE SAME

RELATED APPLICATION

This application is a 35 U.S.C. §371 national phase filing of International Patent Application No. PCT/JP2010/060621, filed Jun. 23, 2010, through which and to which priority is claimed under 35 U.S.C. §119 to Japanese Patent Application No. 2009-163257, filed Jul. 10, 2009.

TECHNICAL FIELD

The present invention relates to a polyfluoroalkylphosphonic acid ester and a process for producing the same. More particularly, the present invention relates to a polyfluoroalkylphosphonic acid ester that can be effectively used, for example, as a starting material for the synthesis of mold-releasing agents or as an additive for lubricating oil; and a process for producing the same.

BACKGROUND ART

Polyfluoroalkylphosphonic acid esters are widely used as starting materials for the synthesis of mold-releasing agents. Compounds having a $C_8$-$C_{12}$ perfluoroalkyl group are most likely to develop mold release performance when used as mold-releasing agents. In particular, $C_8$ telomer compounds of the formula:

are preferably used for this kind of application (see Patent Documents 1 to 4).

Incidentally, it is reported that telomer compounds having a $C_8$-$C_{12}$ perfluoroalkyl group are biologically degraded in the environment and converted to compounds having relatively high bioaccumulation and environmental concentration, causing concerns for exposure during treatment processes, and for release or diffusion from waste, treated substrates, etc., into the environment. Moreover, compounds having a perfluoroalkyl group containing 14 or more carbon atoms are very difficult to handle because of their physical and chemical properties, and hence, such compounds are rarely used in practice.

Furthermore, as for telomer compounds having a perfluoroalkyl group containing 8 or more carbon atoms, generation and incorporation of perfluorooctanoic acids with high bioaccumulation potential is unavoidable during the production of these compounds. For these reasons, companies that produce such telomer compounds have retreated from the production of the compounds or promoted the use of alternative compounds having a perfluoroalkyl group containing 6 or less carbon atoms.

However, compounds having a perfluoroalkyl group containing 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their environmental conditions, such as temperature, humidity, stress, and contact with organic solvents. Consequently, the desired performance cannot be sufficiently achieved, and durability and other properties are affected.

PRIOR ART DOCUMENT

Patent Document

Patent Document 1: JP-B-2-45572
Patent Document 2: JP-B-3-78244
Patent Document 3: JP-B-44923
Patent Document 4: JP-B-4-11366
Patent Document 5: WO 2007/105633 A1

OUTLINE OF THE INVENTION

Problem to be Solved by the Invention

An object of the present invention is to provide a polyfluoroalkylphosphonic acid ester having a perfluoroalkyl group containing 6 or less carbon atoms, which is said to have low bioaccumulation potential, and effectively usable, for example, as a starting material for the synthesis of mold-releasing agents or as an additive for lubricating oil; and to provide a process for producing the same.

Means for Solving the Problem

The present invention provides a polyfluoroalkylphosphonic acid ester represented by the general formula:

wherein R is an alkyl group having 1 to 4 carbon atoms, n is an integer of 1 to 6, a is an integer of 1 to 4, b is an integer of 1 to 3, and c is an integer of 1 to 3.

The polyfluoroalkylphosphonic acid ester is produced by a process comprising reacting a polyfluoroalkyl iodide represented by the general formula:

wherein n is an integer of 1 to 6, a is an integer of 1 to 4, b is an integer of 1 to 3, and c is an integer of 1 to 3, with a trialkyl phosphite represented by the general formula:

wherein R is an alkyl group having 1 to 4 carbon atoms, or by a process comprising reacting a polyfluoro-1-alkene represented by the general formula:

wherein n is an integer of 1 to 6, a is an integer of 1 to 4, and b is an integer of 1 to 3, with a dialkyl phosphite represented by the general formula:

wherein R is an alkyl group having 1 to 4 carbon atoms.

Effect of the Invention

When released into the environment, the polyfluoroalkylphosphonic acid ester of the present invention undergoes HF-elimination in the —$CH_2CF_2$— bonding site of the molecule, and a double bond is formed. The result is then subjected to ozone decomposition etc. to have a structure that is easily decomposed into a compound with low environmental concentration and low bioaccumulation potential. Moreover, the polyfluoroalkylphosphonic acid ester does not produce environmental loading substances (e.g., perfluoroalkyl carboxylic acids) in the production process thereof. Furthermore, as with conventionally used compounds, the polyfluoroalkylphosphonic acid ester can be effectively used, for example, as a starting material for the synthesis of mold-releasing agents or as an additive for lubricating oil.

EMBODIMENTS FOR CARRYING OUT THE INVENTION

The polyfluoroalkylphosphonic acid ester [I] of the present invention is obtained by a process of reacting the polyfluoroalkyl iodide [II] with trialkyl phosphite. The polyfluoroalkyl iodide [II], which is used as a starting material compound, is a known compound, and is disclosed in Patent Document 5.

The polyfluoroalkyl iodide [II], which is used as a starting material for the synthesis of the polyfluoroalkylphosphonic acid ester [I], is produced by the addition reaction of a terminally iodized compound represented by the general formula:

$$C_nF_{2n+1}(CH_2CF_2)_a(CF_2CF_2)_bI \quad [IV]$$

with ethylene. The ethylene addition reaction is carried out in such a manner that the compound [IV] above is subjected to an addition reaction with pressurized ethylene in the presence of a peroxide initiator. The number of addition is 1 to 3, preferably 1, although depending on the reaction conditions. Although the reaction temperature depends on the decomposition temperature of the initiator used, the reaction is generally conducted at about 80 to 120° C.; when a peroxide initiator that decomposes at a low temperature is used, the reaction can be conducted at 80° C. or below.

As a peroxide initiator, di-tert-butly peroxide, di(tert-butylcyclohexyl)peroxy dicarbonate, dicetylperoxy dicarbonate, di-n-propylperoxy dicarbonate, diisopropylperoxy dicarbonate, di-sec-butylperoxy dicarbonate, or the like is used at a ratio of about 1 to 5 mol % with respect to the compound [IV], in terms of the progress and controllability of the reaction.

The terminally iodized compound [IV] is synthesized through a series of the following steps:

(1) A perfluoroalkyl iodide represented by the general formula:

$$C_nF_{2n+1}I \text{ (n: 1 to 6)}$$

is reacted with vinylidene fluoride in the presence of a peroxide initiator as described above in an amount of about 0.1 to 0.5 mol % based on the amount of the starting material compound to obtain a compound represented by the general formula:

$$C_nF_{2n+1}(CH_2CF_2)_aI \quad [V]$$

(2) The compound represented by the general formula [V] is reacted with tetrafluoro ethylene in the presence of a peroxide initiator to thereby obtain a terminally iodized compound represented by the general formula [IV] described above. In the general formula [IV], b is an integer of 1 to 3, preferably 1 or 2. The organic peroxide initiator as mentioned above can be used in this reaction in the same amount as in step (1).

Although the reaction temperature of the addition reaction of vinylidene fluoride or tetrafluoroethylene depends on the decomposition temperature of the initiator used, the use of a peroxide initiator that decomposes at a low temperature allows the reaction to occur at 80° C. or less under low-pressure conditions. The reaction is carried out in the following manner. The perfluoroalkyl iodide $C_nF_{2n+1}I$ or the compound [V] is charged in an autoclave, and the internal temperature is increased to about 10 to 60° C. For example, when the temperature reaches 50° C., a peroxide initiator dissolved in the perfluoroalkyl iodide $C_nF_{2n+1}I$ or the compound [V] is added thereto. When the internal temperature reaches 55° C., for example, vinylidene fluoride or tetrafluoroethylene is added in batches while maintaining the pressure at about 0.1 to 0.6 MPa. After the desired amount of vinylidene fluoride or tetrafluoroethylene is added in batches, aging is carried out, for example, at a temperature of about 55 to 80° C. for about one hour. The amount of vinylidene fluoride or tetrafluoroethylene added affects the number of vinylidene fluoride skeletons a or tetrafluoroethylene skeletons b added by the reaction. Generally, a mixture of various a values and b values is formed.

The fact that these reactions can be carried out at low temperatures indicates that not only energy usage can be reduced, but also corrosion due to hydrofluoric acid etc. in facilities can be prevented, thereby reducing the frequency of updating the facilities. Additionally, since more inexpensiveness materials can be used, capital investment costs can also be kept low, in addition to the decrease in update frequency.

Specific examples of the compound [IV] to which ethylene is added include compounds listed below. These compounds are mixtures of oligomers having various a values and b values. Oligomers that have specific a and b values can be isolated by distilling the mixtures. Oligomers that do not have predetermined a and b values can be reused after isolation or as the mixtures in the reaction of increasing the number of oligomers with vinylidene fluoride or tetrafluoroethylene.

$$C_2F_5(CH_2CF_2)(CF_2CF_2)I$$

$$C_2F_5(CH_2CF_2)(CF_2CF_2)_2I$$

$$C_2F_5(CH_2CF_2)_2(CF_2CF_2)I$$

$$C_2F_5(CH_2CF_2)_2(CF_2CF_2)_2I$$

$$C_2F_5(CH_2CF_2)(CF_2CF_2)_3I$$

$$C_4F_9(CH_2CF_2)(CF_2CF_2)I$$

$$C_4F_9(CH_2CF_2)(CF_2CF_2)_2I$$

$$C_4F_9(CH_2CF_2)_2(CF_2CF_2)I$$

$$C_4F_9(CH_2CF_2)_2(CF_2CF_2)_2I$$

$$C_4F_9(CH_2CF_2)(CF_2CF_2)_3I$$

The polyfluoroalkyl iodide [II] prepared by the addition reaction of the compound [IV] as described above with ethylene can be reacted with trialkyl phosphite $P(OR)_3$ having an alkyl group containing 1 to 4 carbon atoms, such as trimethyl phosphite, triethyl phosphite, tripropyl phosphite, or tributyl phosphite, to perform an RI-elimination reaction, thereby obtaining the target product, i.e., polyfluoroalkylphosphonic acid ester [I]. Without the addition reaction of the compound [IV] with ethylene, the RI-elimination reaction with trialkyl phosphite does not proceed.

In the reaction, about two-fold molar amount of trialkyl phosphite is added to polyfluoroalkyl iodide in the early stage of the reaction, and the reaction is conducted while removing alkyl iodide, which is a by-product, from the reaction system; however, in order to prevent excessive consumption of the phosphite compound because of the reaction with the by-product in the reaction process, it is preferable to subsequently add the phosphite compound in batches.

Moreover, the reaction temperature is not particularly limited in the range of 100° C. to not more than the boiling point of the phosphite compound. However, the reaction takes a longer time at low temperature, whereas large amounts of by-products are produced at high temperature. Accordingly, the temperature is preferably in the range of about 150 to 160° C.

After the completion of the reaction, the reaction mixture is subjected to simple distillation under reduced pressure, and the distillate fraction is washed with water, thereby obtaining a purified reaction product (polyfluoroalkylphosphonic acid ester) with a purity of about 95 to 98 GC %.

The polyfluoroalkylphosphonic acid ester of the formula:

$$C_nF_{2n+1}(CH_2CF_2)_a(CF_2CF_2)_b(CH_2CH_2)P(O)(OR)_2 \quad [I']$$

is also produced by reacting a polyfluoro-1-alkene represented by the general formula:

$$C_nF_{2n+1}(CH_2CF_2)_a(CF_2CF_2)_bCH=CH_2 \quad [III]$$

with a dialkyl phosphite represented by the general formula: $(RO)_2P(O)H$.

The reaction of polyfluoro-1-alkene with dialkyl phosphite $(RO)_2P(O)H$ having a lower alkyl group containing 1 to 4 carbon atoms (e.g., dimethyl phosphite, diethyl phosphite, dipropyl phosphite, or tributyl phosphite) is carried out in the presence of an organic peroxide.

As a peroxide initiator, di-tert-butly peroxide, di(tert-butylcyclohexyl)peroxy dicarbonate, dicetylperoxy dicarbonate, di-n-propylperoxy dicarbonate, diisopropylperoxy dicarbonate, di-tert-butylperoxy dicarbonate, or the like is used at a ratio of about 1 to 5 mol % with respect to the polyfluoro-1-alkene, in terms of the progress and controllability of the reaction.

The polyfluoro-1-alkene [III], which is used as a starting material for this reaction, is obtained by reacting a polyfluoroalkyl iodide represented by the general formula [II] above wherein c is 1, i.e., a compound of the general formula:

$$C_nF_{2n+1}(CH_2CF_2)_a(CF_2CF_2)_b(CH_2CH_2)I \quad [II']$$

with a basic compound to carry out a terminal HI-elimination reaction.

The HI-elimination reaction at position 1 is carried out by reacting the polyfluoroalkyl iodide [II'] with an inorganic basic compound in the presence of a phase transfer catalyst, or by reacting the polyfluoroalkyl iodide [II'] with a nitrogen-containing organic basic compound. The former method is preferably used, so that a polyfluoro-1-alkene having a purity as high as 99% is obtained with high yield. In this case, it is essential to use a phase transfer catalyst in combination with an inorganic basic compound. When no phase transfer catalyst is used, the HI-elimination reaction can hardly proceed.

Examples of inorganic basic compounds include lithium hydroxide, sodium hydroxide, potassium hydroxide, magnesium hydroxide, calcium hydroxide, and other monovalent or divalent metal hydroxides; sodium carbonate, sodium hydrogen carbonate, potassium carbonate, potassium hydrogen carbonate, and other monovalent or divalent metal carbonates; and the like. As a phase transfer catalyst to be used in combination with such an inorganic basic compound, a quaternary onium salt, Crown ether, or the like is used at a ratio of about 0.01 to 10 mol %, preferably about 0.1 to 3 mol %, relative to the inorganic basic compound.

As the quaternary onium salt, at least one of an ammonium salt and a phosphonium salt represented by the following general formulae can be used.

$$(R_1R_2R_3R_4N)^+X^- \quad (R_1R_2R_3R_4P)^+X^-$$

$R_1$ to $R_4$: an alkyl group having 1 to 25 carbon atoms, an alkoxy group, an aryl group, an alkylaryl group, an aralkyl group, or a polyoxyalkylene group; alternatively, two or three groups of these groups can form, together with P or N, a heterocyclic structure.

$X^-$: an anion, such as $Cl^-$, $Br^-$, $I^-$, $HSO_4^-$, $H_2PO_4^-$, $RCOO^-$, $ROSO_2^-$, $RSO^-$, $ROPO_2H^-$, or $CO_3^-$ Examples of nitrogen-containing organic basic compounds include diethylamine, triethylamine, pyridine or derivatives thereof, diethanolamine, triethanolamine, 1,8-diazabicyclo[5.4.0]-7-undecene, diazabicyclononenene, and the like. Preferably, 1,8-diazabicyclo[5.4.0]-7-undecene having low nucleophilicity is used.

When a nitrogen-containing organic basic compound is used, a large amount of polyfluoroalkadiene mixture is produced as a by-product, in addition to the target polyfluoro-1-alkene; however, the polyfluoro-1-alkene and the polyfluoroalkadiene mixture can be separated by fractional distillation based on the difference in vapor temperature during distillation under reduced pressure.

Such an inorganic or organic basic compound is used at a molar ratio of about 0.1 to 10, preferably 0.95 to 2.5, more preferably 1.0 to 1.5, with respect to the polyfluoroalkyl iodide [II'].

EXAMPLES

The following describes the present invention with reference to Examples.

Reference Example 1

In a 1,200-ml autoclave equipped with a stirrer and a thermometer, 603 g (0.99 mol) of a compound of the formula:

$$CF_3(CF_2)_3(CH_2CF_2)(CF_2CF_2)_2I \text{ (99 GC \%)}$$

and 7 g of di-tert-butyl peroxide were charged, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 41 g (1.45 mol) of ethylene was introduced over about 3 hours. The content was collected at an internal temperature of 50° C. or less, thereby obtaining 637 g (yield: 98.8%) of a compound of the formula:

$$CF_3(CF_2)_3(CH_2CF_2)(CF_2CF_2)_2(CH_2CH_2)I \text{ (98 GC \%)}$$

i.e., the formula:

$$C_4F_9CH_2(CF_2)_5CH_2CH_2I.$$

Example 1

In a 1-L, four-necked flask equipped with a thermometer and a receiver for removing low-boiling substances, 500 g (0.78 mol) of the compound of the formula:

$$CF_3(CF_2)_3(CH_2CF_2)(CF_2CF_2)_2(CH_2CH_2)I \text{ (98 GC \%)}$$

obtained in Reference Example 1, and 181 g (1.56 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 91 g (0.78 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 412 g (yield: 78%) of a purified reaction product (96 GC %).

The results of $^1$H-NMR and $^{19}$F-NMR confirmed that the resulting purified reaction product was a compound represented by the following formula:

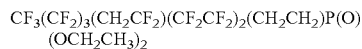

$^1$H-NMR (CD$_3$OD, TMS): δ3.37 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CD$_3$OD, C$_6$F$_6$): ppm −80.2 (CF$_3$)
−124.6 (CF$_3$CF$_2$CF$_2$CF$_2$)
−122.3 (CF$_3$CF$_2$CF$_2$CF$_2$)
−110.0 (CF$_2$CH$_2$CF$_2$)
−110.0 (CF$_2$CH$_2$CF$_2$)
−120.0 (CH$_2$CF$_2$CF$_2$CF$_2$)
−121.6 (CH$_2$CF$_2$CF$_2$CF$_2$)
−122.1 (CF$_2$CF$_2$CH$_2$CH$_2$)
−113.8 (CF$_2$CF$_2$CH$_2$CH$_2$)

Reference Example 2

In a 1,200-ml autoclave equipped with a stirrer and a thermometer, 609 g (1.19 mol) of a compound of the formula:

and 6 g of di-tert-butyl peroxide were charged, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 640 g (yield: 97.3%) of a compound of the formula:

CF$_3$(CF$_2$)$_3$(CH$_2$CF$_2$)(CF$_2$CF$_2$)(CH$_2$CH$_2$)I (97.4 GC %).

Example 2

In a 1-L, four-necked flask equipped with a thermometer and a receiver for removing low-boiling substances, 500 g (0.92 mol) of the compound of the formula:

CF$_3$(CF$_2$)$_3$(CH$_2$CF$_2$)(CF$_2$CF$_2$)(CH$_2$CH$_2$)I (97.4 GC %)

obtained in Reference Example 2, and 213 g (1.84 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 107 g (0.92 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 407 g (yield: 79%) of a purified reaction product (98 GC %).

The results of $^1$H-NMR and $^{19}$F-NMR confirmed that the resulting purified reaction product was a compound represented by the following formula:

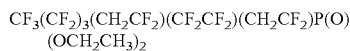

$^1$H-NMR (CD$_3$OD, TMS): δ3.37 (CH$_2$CF$_2$)
2.43 (CH$_2$CH$_2$)
2.07 (CH$_2$CH$_2$)
4.13 (CH$_2$CH$_3$)
1.36 (CH$_2$CH$_3$)
$^{19}$F-NMR (CD$_3$OD, C$_6$F$_6$): ppm −80.2 (CF$_3$)
−124.0 (CF$_3$CF$_2$CF$_2$CF$_2$)
−122.3 (CF$_3$CF$_2$CF$_2$CF$_2$)
−110.3 (CF$_2$CH$_2$CF$_2$)
−109.8 (CF$_2$CH$_2$CF$_2$)
−124.4 (CH$_2$CF$_2$CF$_2$CF$_2$)
−113.1 (CH$_2$CF$_2$CF$_2$CF$_2$)

Reference Example 3

In a 1,200-ml autoclave equipped with a stirrer and a thermometer, 605 g (0.98 mol) of a compound of the formula:

and 7 g of di-tert-butyl peroxide were charged, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 43 g (1.53 mol) of ethylene was introduced over about 3 hours. The content was collected at an internal temperature of 50° C. or less, thereby obtaining 630 g (yield: 98.5%) of a compound of the formula:

CF$_3$(CF$_2$)(CH$_2$CF$_2$)(CF$_2$CF$_2$)$_3$(CH$_2$CH$_2$)I (97.7 GC %).

Example 3

In a 1-L, four-necked flask equipped with a thermometer and a receiver for removing low-boiling substances, 500 g (0.76 mol) of the compound of the formula:

CF$_3$(CF$_2$)(CH$_2$CF$_2$)(CF$_2$CF$_2$)$_3$(CH$_2$CH$_2$)I (97.7 GC %)

obtained in Reference Example 3, and 176 g (1.52 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 88 g (0.76 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 395 g (yield: 77%) of a purified reaction product (96 GC %).

The results of $^1$H-NMR and $^{19}$F-NMR confirmed that the resulting purified reaction product was a compound represented by the following formula:

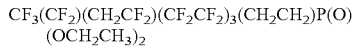

$^1$H-NMR (CD$_3$OD, TMS): δ3.34 (CH$_2$CF$_2$)
2.42 (CH$_2$CH$_2$)
2.07 (CH$_2$CH$_2$)
4.13 (CH$_2$CH$_3$)

1.36 (CH$_2$CH$_3$)
$^{19}$F-NMR (CD$_3$OD, C$_6$F$_6$): ppm −85.3 (CF$_3$)
−114.0 (CF$_3$CF$_2$CH$_2$CF$_2$)
−110.2 (CH$_2$CF$_2$CF$_2$CF$_2$CF$_2$CF$_2$CF$_2$)
−120.0 (CH$_2$CF$_2$CF$_2$CF$_2$CF$_2$CF$_2$CF$_2$)
−119.5 (CH$_2$CF$_2$CF$_2$CF$_2$CF$_2$CF$_2$CF$_2$)
−120.3 (CH$_2$CF$_2$CF$_2$CF$_2$CF$_2$CF$_2$CF$_2$)
−121.4 (CH$_2$CF$_2$CF$_2$CF$_2$CF$_2$CF$_2$CF$_2$)
−122.0 (CH$_2$CF$_2$CF$_2$CF$_2$CF$_2$CF$_2$CF$_2$)
−114.8 (CH$_2$CF$_2$CF$_2$CF$_2$CF$_2$CF$_2$CF$_2$)

Reference Example 4

In a 1,200-ml autoclave equipped with a stirrer and a thermometer, 605 g (1.18 mol) of a compound of the formula:

CF$_3$(CF$_2$)(CH$_2$CF$_2$)(CF$_2$CF$_2$)$_2$I (99.4 GC %)

and 6 g of di-tert-butyl peroxide were charged, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 639 g (yield: 98.0%) of a compound of the formula:

CF$_3$(CF$_2$)(CH$_2$CF$_2$)(CF$_2$CF$_2$)$_2$(CH$_2$CH$_2$)I (97.3 GC %).

Example 4

In a 1-L, four-necked flask equipped with a thermometer and a receiver for removing low-boiling substances, 500 g (0.90 mol) of the compound of the formula:

CF$_3$(CF$_2$)(CH$_2$CF$_2$)(CF$_2$CF$_2$)$_2$(CH$_2$CH$_2$)I (97.3 GC %)

obtained in Reference Example 4, and 208 g (1.80 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 141° C. The distillate fraction was washed with water, thereby obtaining 397 g (yield: 78%) of a purified reaction product (97 GC %).

The results of $^1$H-NMR and $^{19}$F-NMR confirmed that the resulting purified reaction product was a compound represented by the following formula:

CF$_3$(CF$_2$)(CH$_2$CF$_2$)(CF$_2$CF$_2$)$_2$(CH$_2$CH$_2$)P(O)(OCH$_2$CH$_3$)$_2$ $^1$H-NMR (CD$_3$OD, TMS): δ3.34 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CD$_3$OD, C$_6$F$_6$): ppm −85.3 (CF$_3$)
−114.0 (CF$_3$CF$_2$CH$_2$CF$_2$)
−110.1 (CH$_2$CF$_2$CF$_2$CF$_2$CF$_2$CF$_2$)
−120.1 (CH$_2$CF$_2$CF$_2$CF$_2$CF$_2$CF$_2$)
−122.0 (CH$_2$CF$_2$CF$_2$CF$_2$CF$_2$CF$_2$)
−122.4 (CH$_2$CF$_2$CF$_2$CF$_2$CF$_2$CF$_2$)
−113.9 (CH$_2$CF$_2$CF$_2$CF$_2$CF$_2$CF$_2$)

Reference Example 5

In a 1,200-ml autoclave equipped with a stirrer and a thermometer, 610 g (1.48 mol) of a compound of the formula:

CF$_3$(CF$_2$)(CH$_2$CF$_2$)(CF$_2$CF$_2$)I (99.8 GC %)

and 7 g of di-tert-butyl peroxide were charged, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 62 g (2.23 mol) of ethylene was introduced over about 3 hours. The content was collected at an internal temperature of 50° C. or less, thereby obtaining 644 g (yield: 98.0%) of a compound of the formula:

CF$_3$(CF$_2$)(CH$_2$CF$_2$)(CF$_2$CF$_2$)(CH$_2$CH$_2$)I (98.7 GC %).

Example 5

In a 1-L, four-necked flask equipped with a thermometer and a receiver for removing low-boiling substances, 500 g (1.12 mol) of the compound of the formula:

CF$_3$(CF$_2$)(CH$_2$CF$_2$)(CF$_2$CF$_2$)(CH$_2$CH$_2$)I (98.7 GC %)

obtained in Reference Example 5, and 259 g (2.24 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 130 g (1.12 mol) per batch, and the mixture was stirred for 18 hours in total.

After the reaction was completed, the reaction mixture was subjected to simple distillation under reduced pressure at an internal pressure of 0.2 kPa, an internal temperature of 130 to 140° C., and an overhead temperature of 128 to 131° C. The distillate fraction was washed with water, thereby obtaining 405 g (yield: 79%) of a purified reaction product (98 GC %).

The results of $^1$H-NMR and $^{19}$F-NMR confirmed that the resulting purified reaction product was a compound represented by the following formula:

CF$_3$(CF$_2$)(CH$_2$CF$_2$)(CF$_2$CF$_2$)(CH$_2$CH$_2$)P(O)(OCH$_2$CH$_3$)$_2$ $^1$H-NMR (CD$_3$OD, TMS): δ3.34 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CD$_3$OD, C$_6$F$_6$): ppm −85.3 (CF$_3$)
−114.0 (CF$_3$CF$_2$CH$_2$CF$_2$)
−110.4 (CH$_2$CF$_2$CF$_2$CF$_2$)
−122.4 (CH$_2$CF$_2$CF$_2$CF$_2$)
−113.9 (CH$_2$CF$_2$CF$_2$CF$_2$)

Reference Example 6

In a 1,200-ml autoclave equipped with a stirrer and a thermometer, 1,200 g (2.2 mol) of a compound of the formula:

$CF_3(CF_2)_3(CH_2CF_2)(CF_2CF_2)(CH_2CH_2)I$ (99.7 GC %)

and 10 g of di-tert-butyl peroxide were charged, and the autoclave was degassed by a vacuum pump. After the internal temperature was raised to 100° C. by heating, ethylene was sequentially introduced so that the internal pressure was 7.4 MPa. When the internal pressure dropped to 7.0 MPa, ethylene was introduced again to return the pressure to 7.4 MPa; this operation was repeated. While maintaining the internal temperature at 100 to 115° C., 76 g (2.7 mol) of ethylene was introduced over about 6 hours. The content was collected at an internal temperature of 50° C. or less, thereby obtaining 1,237 g (yield: 95.9%) of a compound of the formula:

$CF_3(CF_2)_3(CH_2CF_2)(CF_2CF_2)(CH_2CH_2)_2I$ (98.5 GC %).

Example 6

In a 1-L, four-necked flask equipped with a thermometer and a receiver for removing low-boiling substances, 500 g (0.88 mol) of the compound of the formula:

$CF_3(CF_2)_3(CH_2CF_2)(CF_2CF_2)(CH_2CH_2)_2I$ (98.5 GC %)

obtained in Reference Example 6, and 204 g (1.76 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 102 g (0.88 mol) per batch, and the mixture was stirred for 1.8 hours in total.

After the reaction was completed, the reaction mixture was subjected to simple distillation under reduced pressure at an internal pressure of 0.2 kPa, an internal temperature of 155 to 165° C., and an overhead temperature of 145 to 150° C. The distillate fraction was washed with water, thereby obtaining 385 g (yield: 78%) of a purified reaction product (97 GC %).

The results of $^1$H-NMR and $^{19}$F-NMR confirmed that the resulting purified reaction product was a compound represented by the following formula:

$CF_3(CF_2)_3(CH_2CF_2)(CF_2CF_2)(CH_2CH_2)_2P(O)(OCH_2C_3)_2$ $^1$H-NMR (CD$_3$OD, TMS): δ3.35 (CH$_2$CF$_2$)
2.44 (CH$_2$CH$_2$CH$_2$CH$_2$)
1.63 to 1.74 (CH$_2$CH$_2$CH$_2$CH$_2$)
2.07 (CH$_2$CH$_2$CH$_2$CH$_2$)
4.13 (CH$_2$CH$_3$)
1.36 (CH$_2$CH$_3$)
$^{19}$F-NMR (CD$_3$OD, C$_6$F$_6$): ppm −80.3 (CF$_3$)
−124.0 (CF$_3$CF$_2$CF$_2$CF$_2$)
−122.2 (CF$_3$CF$_2$CF$_2$CF$_2$)
−110.4 (CF$_2$CH$_2$CF$_2$)
−109.7 (CF$_2$CH$_2$CF$_2$)
−124.6 (CH$_2$CF$_2$CF$_2$CF$_2$)
−133.3 (CH$_2$CF$_2$CF$_2$CF$_2$)

Example 7

(1) In a 50-ml glass reactor equipped with a cooling condenser, a thermocouple, and a magnet stirrer, 5 g (7.8 mmol) of 3,3,4,4,5,5,6,6,7,7,9,9,10,10,11,11,12,12,12-nonadecafluoro-1-iodododecane of the formula:  $C_4F_9CH_2(CF_2)_5CH_2CH_2I$ obtained in Reference Example 1 above was suspended in an aqueous solution prepared by dissolving 0.34 g (8.5 mmol) of sodium hydroxide and 0.03 g (0.13 mmol) of tetrabutylammonium chloride in 15 ml of water. The reaction was carried out by continuous stirring for about 72 hours at room temperature.

After the reaction was completed, the lower layer obtained by static phase separation was washed twice with 20 ml of water and then once with a saturated saline solution. The obtained reaction product solution was dehydrated and dried over anhydrous magnesium sulfate. The recovered solution was purified by distillation under reduced pressure, thereby obtaining 3.2 g (yield: 80%) of a product A as a fraction with a vapor temperature of 76 to 77° C./1 kPa (purity: 99%). The structure of the obtained fraction was determined by $^1$H-NMR and $^{19}$F-NMR.

Product A: 3,3,4,4,5,5,6,6,7,7,9,9,10,10,11,11,12,12,12-nonadecafluoro-1-dodecene

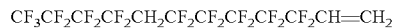
$CF_3CF_2CF_2CF_2CH_2CF_2CF_2CF_2CF_2CH_2CH=CH_2$ $^1$H-NMR (CDCl$_3$, TMS): δ2.89 (CH$_2$CF$_2$)
5.79 (CH=CH$_2$)
5.97 (CH=CH$_2$)
$^{19}$F-NMR (CDCl$_3$, C$_6$F$_6$): ppm −82.1 (CF$_3$)
−126.9 (CF$_3$CF$_2$CF$_2$CF$_2$)
−124.8 (CF$_3$CF$_2$CF$_2$CF$_2$)
−113.2 (CF$_2$CH$_2$CF$_2$)
−113.0 (CF$_2$CH$_2$CF$_2$)
−121.7 (CH$_2$CF$_2$CF$_2$CF$_2$)
−124.2 (CH$_2$CF$_2$CF$_2$CF$_2$)
−124.6 (CF$_2$CF$_2$CH=CH$_2$)
−114.8 (CF$_2$CF$_2$CH=CH$_2$)

(2) In a 1-L, four-necked flask equipped with a thermometer and a condenser, 160 g (1.16 mol) of diethyl phosphite was charged and stirred while heating at 150° C. A mixed solution of 500 g (0.97 mol) of the nonadecafluoro-1-dodecene (product A; 99 GC %) obtained in step (1) above and 2.3 g (16 mmol) of di-tert-butly peroxide was added dropwise thereto. After completion of dropwise addition, the resultant mixture was further stirred for one hour. Thereafter, the reaction mixture was washed with water, and a crude reaction product separated as a lower layer was subjected to simple distillation under reduced pressure at an internal pressure of 0.2 kPa, an internal temperature of 160 to 170° C., and an overhead temperature of 150 to 155° C. Thus, 496 g (yield: 77%) of a purified reaction product (97 GC %) was obtained.

The results of $^1$H-NMR and $^{19}$F-NMR confirmed that the resulting purified reaction product was a compound represented by the following formula:

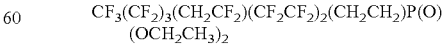
$CF_3(CF_2)_3(CH_2CF_2)(CF_2CF_2)_2(CH_2CH_2)P(O)(OCH_2CH_3)_2$ $^1$H-NMR (CD$_3$OD, TMS): δ3.37 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CD$_3$OD, C$_6$F$_6$): ppm −80.2 (CF$_3$)

-124.6 ($CF_3CF_2CF_2CF_2$)
-122.3 ($CF_3CF_2CF_2CF_2$)
-110.0 ($CF_2CH_2CF_2$)
-110.0 ($CF_2CH_2CF_2$)
-120.0 ($CH_2CF_2CF_2CF_2$)
-121.6 ($CH_2CF_2CF_2CF_2$)
-122.1 ($CF_2CF_2CH_2CH_2$)
-113.8 ($CF_2CF_2CH_2CH_2$)

Example 8

(1) In Example 7, 4.2 g of the polyfluoroalkyl iodide of the following formula:

obtained in Reference Example 2 above was used in place of the compound of the formula:

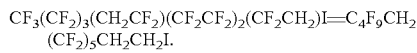

As a result, 2.6 g (yield: 81%) of a compound of the formula: $C_4F_9CH_2(CF_2)_3CH=CH_2$, which was a fraction with a vapor pressure of 63 to 65° C./1 kPa, was obtained as a product B.

Product B: 3,3,4,4,5,5,7,7,8,8,9,9,10,10,10-pentadecafluoro-1-decene

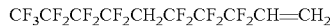

$^1$H-NMR ($CDCl_3$, TMS): δ2.89 ($CH_2CF_2$)
5.79 ($CH=CH_2$)
5.97 ($CH=CH_2$)
$^{19}$F-NMR ($CDCl_3$, $C_6F_6$): ppm -82.0 ($CF_3$)
-126.7 ($CF_3CF_2CF_2$)
-124.9 ($CF_3CF_2CF_2$)
-113.0 ($CF_2CH_2CF_2$)
-111.5 ($CF_2CH_2CF_2$)
-111.8 ($CH_2CF_2CF_2CF_2$)
-114.8 ($CH_2CF_2CF_2CF_2$)

(2) In a 1-L, four-necked flask equipped with a thermometer and a condenser, 200 g (1.45 mol) of diethyl phosphite was charged and stirred while heating at 150° C. A mixed solution of 507 g (1.21 mol) of the pentadecafluoro-1-decene (product B; 99 GC %) obtained in step (1) above and 2.8 g (19 mmol) of di-tert butyl peroxide was added dropwise thereto. After completion of dropwise addition, the resultant mixture was further stirred for one hour. Thereafter, the reaction mixture was washed with water, and a crude reaction product separated as a lower layer was subjected to simple distillation under reduced pressure at an internal pressure of 0.2 kPa, an internal temperature of 145 to 155° C., and an overhead temperature of 138 to 142° C. Thus, 512 g (yield: 74.8%) of a purified reaction product (98 GC %) was obtained.

The results of $^1$H-NMR and $^{19}$F-NMR confirmed that the resulting purified reaction product was a compound represented by the following formula:

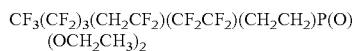

$^1$H-NMR ($CDCl_3$, TMS): δ3.37 ($CH_2CF_2$)
2.43 ($CH_2CH_2$)
2.07 ($CH_2CH_2$)
4.13 ($CH_2CH_3$)
1.36 ($CH_2CH_3$)
$^{19}$F-NMR ($CDCl_3$, $C_6F_6$): ppm -82.0 ($CF_3$)
-124.0 ($CF_3CF_2CF_2$)
-122.3 ($CF_3CF_2CF_2$)
-110.3 ($CF_2CH_2CF_2$)
-109.8 ($CF_2CH_2CF_2$)
-124.4 ($CH_2CF_2CF_2CF_2$)
-113.1 ($CH_2CF_2CF_2CF_2$)

Example 9

(1) In Example 7, 5.0 g of the polyfluoroalkyl iodide of the following formula:

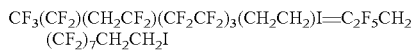

obtained in Reference Example 3 above was used in place of the compound of the formula:

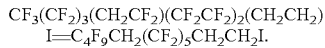

As a result, 2.0 g (yield: 50%) of a compound of the formula: $C_2F_5CH_2(CF_2)_7CH=CH_2$, which was a fraction with a vapor pressure of 75 to 77° C./1 kPa, was obtained as a product C.

Product C: 3,3,4,4,5,5,6,6,7,7,8,8,9,9,11,11,12,12,12-nonadecafluoro-1-dodecene $CF_3CF_2CH_2CF_2CF_2CF_2CF_2CF_2CF_2CH=CH_2$ $^1$H-NMR ($CDCl_3$, TMS): δ2.89 ($CH_2CF_2$)
5.79 ($CH=CH_2$)
5.97 ($CH=CH_2$)
$^{19}$F-NMR ($CDCl_3$, $C_6F_6$): ppm -87.1 ($CF_3$)
-116.8 ($CF_3CF_2CH_2CF_2$)
-113.0 ($CF_3CF_2CH_2CF_2$)
-121.7 ($CH_2CF_2CF_2CF_2$)
-122.7 ($CH_2CF_2CF_2CF_2$)
-124.2 ($CF_2CF_2CF_2CF_2CH=CH_2$)
-122.4 ($CF_2CF_2CF_2CF_2CH=CH_2$)
-122.7 ($CF_2CF_2CF_2CF_2CH=CH_2$)
-114.8 ($CF_2CF_2CF_2CF_2CH=CH_2$)

(2) In a 1-L, four-necked flask equipped with a thermometer and a condenser, 160 g (1.16 mol) of diethyl phosphite was charged and stirred under heating at 150° C. A mixed solution of 500 g (0.95 mol) of the nonadecafluoro-1-dodecene (product C; 97 GC %) obtained in step (1) above and 2.3 g (16 mmol) of di-tert butyl peroxide was added dropwise thereto. After completion of dropwise addition, the resultant mixture was further stirred for one hour. Thereafter, the reaction mixture was washed with water, and a crude reaction product separated as a lower layer was subjected to simple distillation under reduced pressure at an internal pressure of 0.2 kPa, an internal temperature of 160 to 170° C., and an overhead temperature of 150 to 155° C. Thus, 475 g (yield: 74.8%) of a purified reaction product (97 GC %) was obtained.

The results of $^1$H-NMR and $^{19}$F-NMR confirmed that the resulting purified reaction product was a compound represented by the following formula:

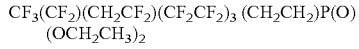

$^1$H-NMR ($CDCl_3$, TMS): δ3.34 ($CH_2CF_2$)
2.42 ($CH_2CH_2$)
2.07 ($CH_2CH_2$)
4.13 ($CH_2CH_3$)
1.36 ($CH_2CH_3$)
$^{19}$F-NMR ($CDCl_3$, $C_6F_6$): ppm -85.3 ($CF_3$)
-114.0 ($CF_3CF_2CH_2CF_2$)
-110.2 ($CH_2CF_2CF_2CF_2CF_2CF_2CF_2CF_2$)
-120.0 ($CH_2CF_2CF_2CF_2CF_2CF_2CF_2CF_2$)
-119.5 ($CH_2CF_2CF_2CF_2CF_2CF_2CF_2CF_2$)
-120.3 ($CH_2CF_2CF_2CF_2CF_2CF_2CF_2CF_2$)
-121.4 ($CH_2CF_2CF_2CF_2CF_2CF_2CF_2CF_2$)
-122.0 ($CH_2CF_2CF_2CF_2CF_2CF_2CF_2CF_2$)
-114.8 ($CH_2CF_2CF_2CF_2CF_2CF_2CF_2CF_2$)

Example 10

(1) In Example 7, 4.2 g of the polyfluoroalkyl iodide of the following formula:

$$CF_3(CF_2)(CH_2CF_2)(CF_2CF_2)_2(CH_2CH_2)I=C_2F_5CH_2(CF_2)_5CH_2CH_2I$$

obtained in Reference Example 4 above was used in place of the compound of the formula:

$$CF_3(CF_2)_3(CH_2CF_2)(CF_2CF_2)_2(CH_2CH_2)I=C_4F_9CH_2(CF_2)_5CH_2CH_2I$$

As a result, 2.5 g (yield: 78%) of a compound of the formula: $C_2F_5CH_2(CF_2)_5CH=CH_2$, which was a fraction with a vapor pressure of 63 to 65° C./1 kPa, was obtained as a product D.

Product D: 3,3,4,4,5,5,6,6,7,7,9,9,10,10,10-pentadecafluoro-1-decene $$CF_3CF_2CH_2CF_2CF_2CF_2CF_2CF_2CH=CH_2$$

$^1$H-NMR (CDCl$_3$, TMS): δ2.89 (CH$_2$CF$_2$)
5.79 (CH=CH$_2$)
5.97 (CH=CH$_2$)
$^{19}$F-NMR (CDCl$_3$, C$_6$F$_6$): ppm −87.1 (CF$_3$)
−116.8 (CF$_3$CF$_2$CH$_2$CF$_2$)
−113.0 (CF$_3$CF$_2$CH$_2$CF$_2$)
−121.5 (CH$_2$CF$_2$CF$_2$CF$_2$)
−124.1 (CH$_2$CF$_2$CF$_2$CF$_2$)
−124.2 (CF$_2$CF$_2$CH=CH$_2$)
−114.8 (CF$_2$CF$_2$CH=CH$_2$)

(2) In a 1-L, four-necked flask equipped with a thermometer and a condenser, 200 g (1.45 mol) of diethyl phosphite was charged and stirred while heating at 150° C. A mixed solution of 500 g (1.18 mol) of the pentadecafluoro-1-decene (product D; 97 GC %) obtained in step (1) above and 2.8 g (19 mmol) of di-tert-butyl peroxide was added dropwise thereto. After completion of dropwise addition, the resultant mixture was further stirred for one hour. Thereafter, the reaction mixture was washed with water, and a crude reaction product separated as a lower layer was subjected to simple distillation under reduced pressure at an internal pressure of 0.2 kPa, an internal temperature of 145 to 155° C., and an overhead temperature of 138 to 141° C. Thus, 505 g (yield: 76.3%) of a purified reaction product (98 GC %) was obtained.

The results of $^1$H-NMR and $^{19}$F-NMR confirmed that the resulting purified reaction product was a compound represented by the following formula:

$$CF_3(CF_2)(CH_2CF_2)(CF_2CF_2)_2(CH_2CH_2)P(O)(OCH_2CH_3)_2$$

$^1$H-NMR (CDCl$_3$, TMS): δ3.34 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CDCl$_3$, C$_6$F$_6$): ppm −85.3 (CF$_3$)
−114.0 (CF$_3$CF$_2$CH$_2$CF$_2$)
−110.1 (CH$_2$CF$_2$CF$_2$CF$_2$CF$_2$CF$_2$)
−120.1 (CH$_2$CF$_2$CF$_2$CF$_2$CF$_2$CF$_2$)
−122.0 (CH$_2$CF$_2$CF$_2$CF$_2$CF$_2$CF$_2$)
−122.4 (CH$_2$CF$_2$CF$_2$CF$_2$CF$_2$CF$_2$)
−113.9 (CH$_2$CF$_2$CF$_2$CF$_2$CF$_2$CF$_2$)

Example 11

(1) In Example 7, 3.4 g of the polyfluoroalkyl iodide of the following formula:

$$CF_3(CF_2)(CH_2CF_2)(CF_2CF_2)(CH_2CH_2)I=C_2F_5CH_2(CF_2)_3CH_2CH_2I$$

obtained in Reference Example 5 above was used in place of the compound of the formula:

$$CF_3(CF_2)_3(CH_2CF_2)(CF_2CF_2)_2(CH_2CH_2)I=C_4F_9CH_2(CF_2)_5CH_2CH_2I.$$

As a result, 2.1 g (yield: 87%) of a compound of the formula: $C_2F_5CH_2(CF_2)_3CH=CH_2$, which was a fraction with a vapor pressure of 52 to 55° C./1 kPa, was obtained as a product E.

Product E: 3,3,4,4,5,5,7,7,8,8,8-undecafluoro-1-octene $$CF_3CF_2CH_2CF_2CF_2CF_2CH=CH_2$$

$^1$H-NMR (CDCl$_3$, TMS): δ2.89 (CH$_2$CF$_2$)
5.79 (CH=CH$_2$)
5.97 (CH=CH$_2$)
$^{19}$F-NMR (CDCl$_3$, C$_6$F$_6$): ppm −87.1 (CF$_3$)
−116.8 (CF$_3$CF$_2$CH$_2$CF$_2$)
−111.6 (CF$_3$CF$_2$CH$_2$CF$_2$)
−111.9 (CF$_2$CF$_2$CH=CH$_2$)
−114.8 (CF$_2$CF$_2$CH=CH$_2$)

(2) In a 1-L, four-necked flask equipped with a thermometer and a condenser, 262 g (1.90 mol) of diethyl phosphite was charged and stirred while heating at 150° C. A mixed solution of 500 g (1.58 mol) of the undecafluoro-1-octene (product E; 98 GC %) obtained in step (1) above and 3.7 g (25 mmol) of di-tert-butyl peroxide was added dropwise thereto. After completion of dropwise addition, the resultant mixture was further stirred for one hour. Thereafter, the reaction mixture was washed with water, and a crude reaction product separated as a lower layer was subjected to simple distillation under reduced pressure at an internal pressure of 0.2 kPa, an internal temperature of 130 to 140° C., and an overhead temperature of 128 to 131° C. Thus, 547 g (yield: 75.7%) of a purified reaction product (98 GC %) was obtained.

The results of $^1$H-NMR and $^{19}$F-NMR confirmed that the resulting purified reaction product was a compound represented by the following formula:

$$CF_3(CF_2)(CH_2CF_2)(CF_2CF_2)(CH_2CH_2)P(O)(OCH_2CH_3)_2$$

$^1$H-NMR (CDCl$_3$, TMS): δ3.34 (CH$_2$CF$_2$)
2.42 (CH$_2$CH$_2$)
2.07 (CH$_2$CH$_2$)
4.13 (CH$_2$CH$_3$)
1.36 (CH$_2$CH$_3$)
$^{19}$F-NMR (CDCl$_3$, C$_6$F$_6$): ppm −85.3 (CF$_3$)
−114.0 (CF$_3$CF$_2$CH$_2$CF$_2$)
−110.4 (CH$_2$CF$_2$CF$_2$CF$_2$)
−122.4 (CH$_2$CF$_2$CF$_2$CF$_2$)
−113.9 (CH$_2$CF$_2$CF$_2$CF$_2$)

Reference Example 7

The phosphonic acid ester (3 wt. %) obtained in Example 1 or 7 was added to a base oil of the formula: $C_nF_{2n+1}(CF_2CF_2CF_2O)_mC_nF_{2n+1}$ (viscosity at 40° C.: 210 mm$^2$/s), and the mixture was sufficiently stirred under heating. After the mixture was stored at 25° C. for 24 hours, the solubility of the phosphonic acid ester in the base oil was visually observed. Although stagnation and slight white-muddying were observed, the phosphonic acid ester was dissolved into an almost transparent solution.

In addition, 1 wt. % of the above phosphonic acid ester was added to each of the above base oils, and the mixture was sufficiently stirred while heating. Thereafter, rust resistance was evaluated according to a rust-prevention performance test for lubricating oil type rust preventive oil (lubrication test) prescribed in JIS K2246 (rust preventive oil). The evaluation was carried out by counting the number of rust spots in a test piece after 240 hours. The result was such that the number of rust spots was in the range of 1 to 10, showing somewhat better rust resistance.

The invention claimed is:

1. A process for producing a polyfluoroalkylphosphonic acid ester represented by the general formula:

$$C_nF_{2n+1}(CH_2CF_2)_a(CF_2CF_2)_b(CH_2CH_2)P(O)(OR)_2 \quad [I']$$

wherein R is an alkyl group having 1 to 4 carbon atoms, n is an integer of 1 to 6, a is an integer of 1 to 4, and b is an integer of 1 to 3, the process comprising subjecting a mixed solution of polyfluoro-1-alkene represented by the general formula:

$$C_nF_{2n+1}(CH_2CF_2)_a(CF_2CF_2)_bCH=CH_2 \quad [III]$$

wherein n, a, and b are as defined above, and an organic peroxide to an addition reaction with a dialkyl phosphite represented by the general formula:

$$(RO)_2P(O)H$$

wherein R is as defined above.

2. The process for producing a polyfluoroalkylphosphonic acid ester according to claim 1, wherein the polyfluoro-1-alkene [III] is a compound obtained by a terminal HI-elimination reaction of a polyfluoroalkyl iodide with an inorganic basic compound in the presence of a phase transfer catalyst represented by the general formula:

$$C_nF_{2n+1}(CH_2CF_2)_a(CF_2CF_2)_b(CH_2CH_2)I \quad [II]$$

wherein n is an integer of 1 to 6, a is an integer of 1 to 4, and b is an integer of 1 to 3.

3. The process for producing a polyfluoroalkylphosphonic acid ester according to claim 1, wherein a yield of the polyfluoroalkylphosphonic acid ester based upon the use of the dialkyl phosphite is 63.2 to 66.0%.

* * * * *